United States Patent
Ahmed et al.

(10) Patent No.: US 11,897,849 B1
(45) Date of Patent: Feb. 13, 2024

(54) N'-(2-(5-PHENYL-1,3,4-OXADIAZOL-2-YLTHIO)ACETOXY)-1-NAPHTHIMIDAMIDE AS ANTIMICROBIAL COMPOUND

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Antar Ahmed Abdelhamid Ahmed, Sohag (EG); Amer A. Amer, Sohag (EG)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/377,887

(22) Filed: Oct. 9, 2023

(51) Int. Cl.
*C07D 271/113* (2006.01)
*A61P 31/04* (2006.01)
*A61P 31/10* (2006.01)

(52) U.S. Cl.
CPC .......... *C07D 271/113* (2013.01); *A61P 31/04* (2018.01); *A61P 31/10* (2018.01)

(58) Field of Classification Search
CPC ....... C07D 271/113; A61P 31/04; A61P 31/10
USPC ........................................ 514/363
See application file for complete search history.

(56) References Cited

U.S. PATENT DOCUMENTS 11,679,093 B2   6/2023   Benam

FOREIGN PATENT DOCUMENTS

IN   342249 A1   7/2020

OTHER PUBLICATIONS

Al-Azzawi, et al. "Synthesis and antimicrobial screening of new naphthalimides linked to oxadiazole, thiadiazole and triazole cycles." Carbon 5 (2014): 19.

Maroufal-Azzawi. "Synthesis, Characterization and evaluation of antibacterial activity of several new 3, 4-dimethyl maleimides and 1, 8-naphthalimides containing 1, 3, 4-oxadiazole ring." Al-Nahrain Journal of Science 14.1 (2011).

Khan, et al. "Synthesis, Characterization and Antimicrobial Screening of Some Bioactive 1, 8-Naphthalimide Derivatives." Al Mustansiriyah Journal of Pharmaceutical Sciences 14.2 (2014): 33-47.

El-Sayed, et al. "Synthesis and Antimicrobial Activity of New 1, 2, 3-Triazolopyrimidine Derivatives and Their Glycoside and Acyclic Nucleoside Analogs." Journal of Heterocyclic Chemistry 49.3 (2012): 607-612.

Al-Amiery. "Antimicrobial and antioxidant activities of new metal complexes derived from (E)-3-((5-phenyl-1, 3, 4-oxadiazol-2-ylimino) methyl) naphthalen-2-ol." Medicinal Chemistry Research 21 (2012): 3204-3213.

*Primary Examiner* — Kristin A Vajda
(74) *Attorney, Agent, or Firm* — Nath, Goldberg & Meyer; Richard C. Litman

(57) ABSTRACT

A N'-(2-(5-phenyl-1,3,4-oxadiazol-2-ylthio)acetoxy)-1-naphthimidamide compound, its synthesis, and its use as an anti-microbial agent.

17 Claims, No Drawings

N'-(2-(5-PHENYL-1,3,4-OXADIAZOL-2-YLTHIO)ACETOXY)-1-NAPHTHIMIDAMIDE AS ANTIMICROBIAL COMPOUND

BACKGROUND

1. Field

The present disclosure relates to the compound N'-(2-(5-phenyl-1,3,4-oxadiazol-2-ylthio)acetoxy)-1-naphthimidamide, its synthesis, and its use as an anti-microbial agent.

2. Description of the Related Art

There remains an ongoing need for new therapeutically active agents for treating a variety of diseases, disorders, and conditions including, but not limited to, various forms of cancer, various microbial infections, and the like.

Further, once such new therapeutically active agents are designed and/or discovered, they are often difficult to synthesize and/or prepare. It remains difficult to prepare such compounds without using solvents, to obtain a high yield, based on efficient reaction times, which are easy to use, and which involve a catalyst that can be recycled.

Bacterial infection remains a significant threat to human life due to its increasing resistance to conventional antibiotics, which is a growing public health concern. As a result, there is a critical need to create new antimicrobial agents with potent anti-drug-resistant microorganism activity. That is why antimicrobial agent investigations are so critical and should always be up to date.

The chemistry of heterocycles lies at the heart of drug discovery. Investigation of fortunate organic compounds for drug discovery has been a rapidly emerging theme in medicinal chemistry. 1,3,4-oxadiazole nucleus is found to possess a number of biological activities such as anticancer, antimicrobial, antidiabetic, anti-inflammatory, antiviral, antileishmanial, antitumor, anthelmintic, anticonvulsant, analgesic, anti-oxidant and antiviral.

Furthermore, the amidine functional group is an important structural element of compounds with various biological activities such as antidegenerative, anticancer, antiplatelet, anti-HIV, antibacterial, and antifungal.

Moreover, amidoxime derivatives exhibited notable biological activities as anti-inflammatory, antihyperglycemic, antimycobacterial, serotonergic inhibitory, muscarinic agonist, and peptide inhibitory activities.

Bacterial infection remains a significant threat to human life due to its increasing resistance to conventional antibiotics, which is a growing public health concern. As a result, there is a critical need to create new antimicrobial agents with potent anti-drug-resistant microorganism activity.

Thus, new molecules having desired therapeutic activities and solving the aforementioned problems are desired.

SUMMARY

The present subject matter relates to a N'-(2-(5-phenyl-1,3,4-oxadiazol-2-ylthio)acetoxy)-1-naphthimidamide compound. The product can be acquired in high yields (average about 70%) using a one-pot three-component reaction using 2-(5-phenyl-1,3,4-oxadiazol-2-ylthio)acetic acid in acetonitrile, carbonyldiimidazole (CDI), and N'-hydroxynaphthalene-1-carboximidamide. The compound N'-(2-(5-phenyl-1,3,4-oxadiazol-2-ylthio)acetoxy)-1-naphthimidamide (3) has demonstrated anti-microbial activity.

In an embodiment, the present subject matter relates to a N'-(2-(5-phenyl-1,3,4-oxadiazol-2-ylthio)acetoxy)-1-naphthimidamide compound having the formula I.

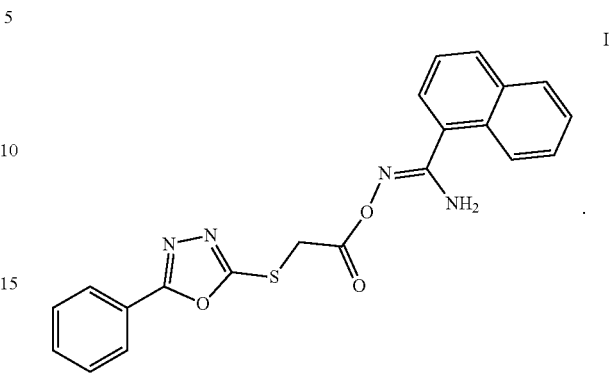

In another embodiment, the present subject matter relates to a pharmaceutically acceptable composition comprising a therapeutically effective amount of the N'-(2-(5-phenyl-1,3,4-oxadiazol-2-ylthio)acetoxy)-1-naphthimidamide compound and a pharmaceutically acceptable carrier.

In a further embodiment, the present subject matter relates to a method of treating a microbial infection in a patient comprising administering to a patient in need thereof a therapeutically effective amount of the N'-(2-(5-phenyl-1,3,4-oxadiazol-2-ylthio)acetoxy)-1-naphthimidamide compound.

In one more embodiment, the present subject matter relates to a method of making the N'-(2-(5-phenyl-1,3,4-oxadiazol-2-ylthio)acetoxy)-1-naphthimidamide compound, the method comprising: adding carbonyldiimidazole (CDI) to a solution of 2-(5-phenyl-1,3,4-oxadiazol-2-ylthio)acetic acid in acetonitrile to obtain a reaction mixture; stirring the reaction mixture a first time; adding N'-hydroxynaphthalene-1-carboximidamide to the reaction mixture; stirring the reaction mixture a second time; filtering and washing a formed precipitate with acetonitrile; drying and recrystallizing using acetonitrile; and obtaining the N'-(2-(5-phenyl-1,3,4-oxadiazol-2-ylthio)acetoxy)-1-naphthimidamide compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats, and the like.

"Patient" as used herein refers to a subject in need of treatment of a condition, disorder, or disease, such as a microbial infection.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a N'-(2-(5-phenyl-1,3,4-oxadiazol-2-ylthio)acetoxy)-1-naphthimidamide compound. The product can be acquired in high yields (average about 70%) using a one-pot three-component reaction using 2-(5-phenyl-1,3,4-oxadiazol-2-ylthio)acetic acid in acetonitrile, carbonyldiimidazole (CDI), and N'-hydroxynaphthalene-1-carboximidamide. The compound N'-(2-(5-phenyl-1,3,4-oxadiazol-2-ylthio)acetoxy)-1-naphthimidamide (3) is likely to have a high anti-microbial effect.

In an embodiment, the present subject matter relates to a N'-(2-(5-phenyl-1,3,4-oxadiazol-2-ylthio)acetoxy)-1-naphthimidamide compound having the formula I.

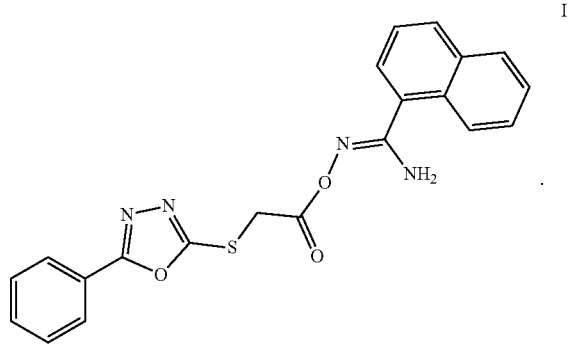 [SMILES: N/C(=N\OC(=O)CSc1nnc(-c2ccccc2)o1)c1cccc2ccccc12 ; "."]

In certain embodiments, the N'-(2-(5-phenyl-1,3,4-oxadiazol-2-ylthio)acetoxy)-1-naphthimidamide compound can be obtained as crystals. In further embodiments, the N'-(2-(5-phenyl-1,3,4-oxadiazol-2-ylthio)acetoxy)-1-naphthimidamide compound can have a melting point of about 177° C. to about 178° C.

In another embodiment, the present subject matter relates to a pharmaceutically acceptable composition comprising a therapeutically effective amount of the N'-(2-(5-phenyl-1,3,4-oxadiazol-2-ylthio)acetoxy)-1-naphthimidamide compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for cancer or a microbial infection. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of a microbial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

In a further embodiment, the present subject matter relates to a method of treating a microbial infection in a patient comprising administering to a patient in need thereof a therapeutically effective amount of the N'-(2-(5-phenyl-1,3,4-oxadiazol-2-ylthio)acetoxy)-1-naphthimidamide compound.

In certain embodiments in this regard, the microbial infection can be caused by one or more bacteria or fungi.

In an embodiment, the microbial infection can be caused by one or more gram positive bacteria. In this regard, non-limiting examples of the one or more gram positive bacterial strains causing the microbial infection include *Bacillus cereus* and *Staphylococcus aureus*. In another embodiment, the microbial infection can be caused by one or more gram negative bacteria. In this regard, non-limiting examples of the one or more gram-negative bacterial strains causing the microbial infection include *Pseudomonas aeruginosa* and *Escherichia coli*. In a further embodiment, the microbial infection can be caused by one or more fungi. In this regard, non-limiting examples of the one or more fungi causing the microbial infection include *Aspergillus flavus* and *Chrysosporium keratinophilum*. Any combination of any of the foregoing are further contemplated herein.

In one more embodiment, the present subject matter relates to a method of making the N'-(2-(5-phenyl-1,3,4-oxadiazol-2-ylthio)acetoxy)-1-naphthimidamide compound, the method comprising: adding carbonyldiimidazole (CDI) to a solution of 2-(5-phenyl-1,3,4-oxadiazol-2-ylthio)acetic acid in acetonitrile to obtain a reaction mixture; stirring the reaction mixture a first time; adding N'-hydroxynaphthalene-1-carboximidamide to the reaction mixture; stirring the reaction mixture a second time; filtering and washing a formed precipitate with acetonitrile; drying and recrystallizing using acetonitrile; and obtaining the N'-(2-(5-phenyl-1,3,4-oxadiazol-2-ylthio)acetoxy)-1-naphthimidamide compound.

The present production methods can be further seen by referring to the following Scheme 1:

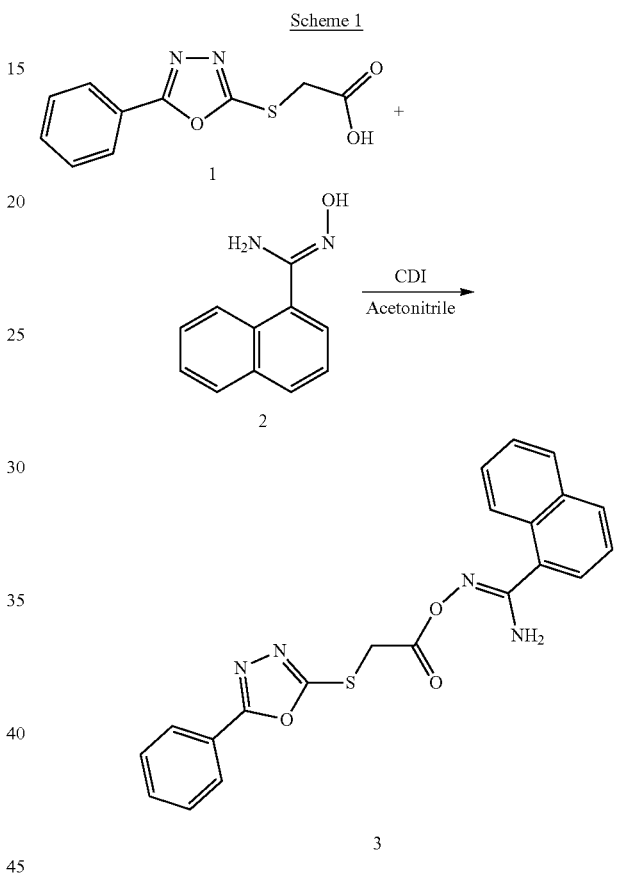

In an embodiment of the present production methods, the stirring 2-(5-phenyl-1,3,4-oxadiazol-2-ylthio)acetic acid in acetonitrile and carbonyldiimidazole, or the stirring the first time, can last for between about 25 minutes and 35 minutes, or for about 30 minutes.

In another embodiment of the present production methods, the stirring of the 2-(5-phenyl-1,3,4-oxadiazol-2-ylthio) acetic acid in acetonitrile, carbonyldiimidazole, and N'-hydroxynaphthalene-1-carboxiiidarnide, or the stirring the second time, can last for at least about 6 hours.

In a further embodiment of the present production methods, the reaction mixture can be stirred at room temperature.

In another embodiment of the present production methods, the 2-(5-phenyl-1,3,4-oxadiazol-2-ylthio)acetic acid and carbonyldiimidazole can be added in an about 2:2.4 molar ratio.

In a further embodiment of the present production methods, the 2-(5-phenyl-1,3,4-oxadiazol-2-ylthio)acetic acid, carbonyldiimidazole, and N-hydroxynaphthalene-1-carboximidamide can be added in an about 2:2.4:2 molar ratio.

In an additional embodiment of the present production methods, the N'-(2-(5-phenyl-1,3,4-oxadiazol-2-ylthio)acetoxy)-1-naphthimidamide can be obtained in a yield of about 70%.

The following examples relate to various methods of manufacturing the specific compounds and application of the same, as described herein. All compound numbers expressed herein are with reference to the synthetic pathway FIGURES shown above.

EXAMPLES

Example 1

Preparation of N'-(2-(5-phenyl-1,3,4-oxadiazol-2-ylthio)acetoxy)-1-naphthimidamide To a solution of 2-(5-phenyl-1,3,4-oxadiazol-2-ylthio) acetic acid (1) (0.47 g, 0.002 mol) in 60 ml acetonitrile, CDI (0.39 g, 0.0024 mole) was added and the reaction mixture was allowed to stir at room temperature for 30 min. Then, N'-hydroxynaphthalene-1-carboximidamide (2) (0.37 g, 0.002 mole) was added and stirring continued for a further 6 hours. After completion of the reaction (as monitored by TLC), the formed precipitate was collected by filtration, washed several times with cold acetonitrile, dried and recrystallized from acetonitrile to afford N'-(2-(5-phenyl-1, 3,4-oxadiazol-2-ylthio)acetoxy)-1-naphthimidamide (3). The elemental analysis can be seen as follows:

Mp. 177-178° C. Yield=70%. FTIR (KBr, cm-1) 3348, 3251 (NH$_2$), 3055 (CHarom.), 2954 (CHaliph.), 1719 (C=O); $^1$H-NMR (CDCl$_3$, 400 MHz): 8.00 (d., J=8 Hz, 1H, CHarom.), 7.91-7.77 (m., 3H, CHarom.), 7.58-7.35 (m., 8H, CHarom.), 5.67 (br.s., 2H, NH$_2$), 3.86 (s., 2H, CH$_2$).; Analysis: calculated for C$_{21}$H$_{16}$N$_4$O$_3$S (404.44): C, 62.36; H, 3.99; N, 13.85%. Found: C, 62.49; H, 3.81; N, 13.79%.

Example 2

Anti-Microbial Activity

Antimicrobial Testing Method

The agar plate disc-diffusion method was applied. Sterilized filter papers (6 mm in diameter) were wetted with 10 μL of a solution of N'-(2-(5-phenyl-1,3,4-oxadiazol-2-ylthio) acetoxy)-2-naphthimidamide (3) to be tested, containing 10 mg/mL in DMSO, and the discs were allowed to air dry. The discs were then placed onto the surface of agar plates (nutrient agar for bacteria and Sabouraud's dextrose agar for fungi) seeded with the test organism. Each plate contained 15 of the agar medium, previously seeded with 0.2 mL of the broth culture of each organism pre-grown for 18 hours. The plates were incubated at 37° C. for 48 hours and 72 hours for fungi. The inhibition zones were measured in mm. Discs impregnated with DMSO were used as a control, and their inhibition zone was subtracted from the tested compound's actual inhibition zone.

Antimicrobial Activity

The N'-(2-(5-phenyl-1,3,4-oxadiazol-2-ylthio)acetoxy)-1-naphthimidamide compound (3) demonstrated high antimicrobial activities. The N'-(2-(5-phenyl-1,3,4-oxadiazol-2-ylthio)acetoxy)-1-naphthimidamide (3) compound demonstrated excellent antimicrobials activities against different microbes. Their antibacterial screened against gram positive bacteria namely *Bacillus cereus* and *Staphylococcus aureus* and gram-negative bacterial strains namely *Pseudomonas aeruginosa* and *Escherichia coli* is shown in Table 1 using ciprofloxacin as a reference point.

TABLE 1

| | Type | | | | | | | | | | |
|---|---|---|---|---|---|---|---|---|---|---|---|
| | Gram positive | | | | | | Gram negative | | | | |
| | *Bacillus Cereus* | | | *Staphylococcus aureus* | | | *Pseudomonas aeruginosa* | | | *Escherichia coli* | | |
| Comp | A | B | C | A | B | C | A | B | C | A | B | C |
| 3 | 19 | 26 | 35 | 29 | 35 | 44 | 22 | 30 | 37 | 35 | 39 | 45 |
| Control | 0 | 0 | 0 | 0 | 0 | 0 | 0 | 0 | 0 | 0 | 0 | 0 |
| Cip. | 29 | 30 | 42 | 43 | 44 | 53 | 29 | 30 | 53 | 30 | 39 | 60 |

A = concentration of comp. = 10,000 μL, B = concentration of comp. = 30.000 μL, C = concentration of comp. = 50,000 μL The antifungal activity of N'-(2-(5-phenyl-1,3,4-oxadiazol-2-ylthio)acetoxy)-1-naphthimidamide screened against *Aspergillus flavus* and *Chrysosporium keratinophilum* is shown in Table 2, again using ciprofloxacin as a reference point.

TABLE 2

| | Fungal | | | | | |
|---|---|---|---|---|---|---|
| | *Aspergillus flavus* | | | *Chrysosporium keratinophilum* | | |
| Comp | A | B | C | A | B | C |
| 3 | 15 | 22 | 30 | 29 | 37 | 43 |
| Control | 0 | 0 | 0 | 0 | 0 | 0 |

Antifungal activity of N'-(2-(5-phenyl-1,3,4-oxadiazol-2-ylthio)acetoxy)-1-naphthimidamide (3) against *Aspergillus flavus* and *Chrysosporium keratinophilum* by measuring inhibition zone.

It is to be understood that the N'-(2-(5-phenyl-1,3,4-oxadiazol-2-ylthio)acetoxy)-1-naphthimidamide compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A N'-(2-(5-phenyl-1,3,4-oxadiazol-2-ylthio)acetoxy)-1-naphthimidamide compound having the formula I:

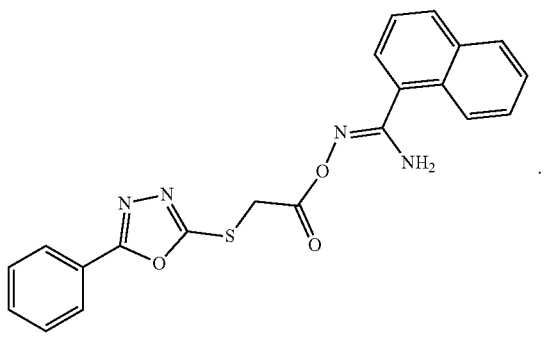

2. The N'-(2-(5-phenyl-1,3,4-oxadiazol-2-ylthio)acetoxy)-1-naphthimidamide compound of claim 1, wherein the compound is obtained as crystals.

3. The N'-(2-(5-phenyl-1,3,4-oxadiazol-2-ylthio)acetoxy)-1-naphthimidamide compound of claim 1, having a melting point of about 177° C. to about 178° C.

4. A pharmaceutically acceptable composition comprising a therapeutically effective amount of the N'-(2-(5-phenyl-1,3,4-oxadiazol-2-ylthio)acetoxy)-1-naphthimidamide compound of claim 1 and a pharmaceutically acceptable carrier.

5. A method of treating a microbial infection in a patient comprising administering to a patient in need thereof a therapeutically effective amount of the N'-(2-(5-phenyl-1,3,4-oxadiazol-2-ylthio)acetoxy)-1-naphthimidamide compound of claim 1.

6. The method of treating the microbial infection of claim 5, wherein the microbial infection is caused by one or more bacteria or fungi.

7. The method of treating the microbial infection of claim 6, wherein the microbial infection is caused by one or more Gram-negative bacterial strains selected from the group consisting of *Escherichia coli* and *Pseudomonas aeruginosa*; one or more Gram-positive bacterial strains that is *Bacillus cereus; Staphylococcus aureus*; or any combination thereof.

8. The method of treating the microbial infection of claim 6, wherein the microbial infection is caused by *Bacillus Cereus* and *Staphylococcus aureus*.

9. The method of treating the microbial infection of claim 6, wherein the microbial infection is caused by *Escherichia coli* or *Pseudomonas aeruginosa*.

10. The method of treating the microbial infection of claim 6, wherein the microbial infection is caused by one or more fungi selected from the group consisting of *Aspergillusflavus* and *Chrysosporium keratinophilum*.

11. A method of making the N'-(2-(5-phenyl-1,3,4-oxadiazol-2-ylthio)acetoxy)-1-naphthimidamide compound of claim 1, the method comprising:
  adding carbonyldiimidazole to a solution of 2-(5-phenyl-1,3,4-oxadiazol-2-ylthio)acetic acid in acetonitrile to obtain a reaction mixture;
  stirring the reaction mixture a first time;
  adding N'-hydroxynaphthalene-1-carboximidamide to the reaction mixture;
  stirring the reaction mixture a second time;
  filtering and washing a formed precipitate with acetonitrile;
  drying and recrystallizing using acetonitrile; and
  obtaining the N'-(2-(5-phenyl-1,3,4-oxadiazol-2-ylthio)acetoxy)-1-naphthimidamide compound.

12. The method of making the N'-(2-(5-phenyl-1,3,4-oxadiazol-2-ylthio)acetoxy)-1-naphthimidamide compound of claim 11, wherein the reaction mixture is stirred the first time for between about 25 minutes and 35 minutes.

13. The method of making the N'-(2-(5-phenyl-1,3,4-oxadiazol-2-ylthio)acetoxy)-1-naphthimidamide of claim 11, wherein the reaction mixture is stirred the second time for at least about 6 hours.

14. The method of making the N'-(2-(5-phenyl-1,3,4-oxadiazol-2-ylthio)acetoxy)-1-naphthimidamide compound of claim 11, wherein the reaction mixture is stirred at room temperature.

15. The method of making the N'-(2-(5-phenyl-1,3,4-oxadiazol-2-ylthio)acetoxy)-1-naphthimidamide compound of claim 11, wherein the 2-(5-phenyl-1,3,4-oxadiazol-2-ylthio)acetic acid and carbonyldiimidazole are added in an about 1:1 molar ratio.

16. The method of making the N'-(2-(5-phenyl-1,3,4-oxadiazol-2-ylthio)acetoxy)-1-naphthimidamide compound of claim 11, wherein the 2-(5-phenyl-1,3,4-oxadiazol-2-ylthio)acetic acid and N'-hydroxynaphthalene-1-carboximidamide are added in an about 1:1 molar ratio.

17. The method of making the N'-(2-(5-phenyl-1,3,4-oxadiazol-2-ylthio)acetoxy)-1-naphthimidamide compound of claim 11, wherein N'-(2-(5-phenyl-1,3,4-oxadiazol-2-ylthio)acetoxy)-1-naphthimidamide compound is obtained in an about 70% yield.

* * * * *